United States Patent
Ladriere et al.

(10) Patent No.: US 9,138,006 B2
(45) Date of Patent: Sep. 22, 2015

(54) SACCHAROMYCES CEREVISIAE STRAINS SUITABLE FOR THE PRODUCTION OF BAKER'S YEASTS WHICH ARE OSMOTOLERANT AND WHICH EXHIBIT INTRINSIC RESISTANCE TO WEAK ORGANIC ACIDS, METHODS FOR THE PREPARATION THEREOF AND USES

(71) Applicant: LESAFFRE ET COMPAGNIE, Paris (FR)

(72) Inventors: Jean-Marc Ladriere, Querenaing (FR); Jean-Charles Bartolucci, Saint Andre-lez-Lille (FR); Fabienne Sucher, Marcq-en-Baroeul (FR); Benoit Thomas, Marquette-lez-Lille (FR)

(73) Assignee: LESAFFRE ET COMPAGNIE, Paris (FR)

( * ) Notice: Subject to any disclaimer, the term of this patent is extended or adjusted under 35 U.S.C. 154(b) by 64 days.

(21) Appl. No.: 13/965,923

(22) Filed: Aug. 13, 2013

(65) Prior Publication Data
US 2014/0010919 A1  Jan. 9, 2014

Related U.S. Application Data

(63) Continuation-in-part of application No. PCT/FR2011/051550, filed on Jul. 1, 2011.

(30) Foreign Application Priority Data

Feb. 18, 2011 (FR) .................................. 11 51354

(51) Int. Cl.
| | |
|---|---|
| A21D 8/04 | (2006.01) |
| C12N 15/81 | (2006.01) |
| A21D 2/14 | (2006.01) |
| C12N 1/18 | (2006.01) |
| C12N 15/01 | (2006.01) |

(52) U.S. Cl.
CPC ............... *A21D 8/047* (2013.01); *A21D 2/145* (2013.01); *C12N 1/18* (2013.01); *C12N 15/01* (2013.01); *C12N 15/81* (2013.01)

(58) Field of Classification Search
CPC ....... A21D 8/047; A21D 2/145; C12N 15/81; C12N 15/01; C12N 1/18
USPC .................................. 426/62, 549; 435/254.21
See application file for complete search history.

(56) References Cited

U.S. PATENT DOCUMENTS

| 4,318,929 A | 3/1982 | Clement et al. |
|---|---|---|
| 4,318,991 A * | 3/1982 | Hill .............................. 435/245 |
| 4,346,115 A | 8/1982 | Clement et al. |
| 6,521,272 B1 * | 2/2003 | Ando et al. ..................... 426/62 |

FOREIGN PATENT DOCUMENTS

| CN | 101 418 265 | 4/2009 |
|---|---|---|
| EP | 0 645 094 | 3/1995 |
| EP | 1 559 322 | 8/2005 |
| FR | 2 971 790 | 8/2012 |
| GB | 2 115 833 | 9/1983 |
| WO | WO 96/38538 | 12/1996 |
| WO | WO 99/51746 | 10/1999 |
| WO | WO 2009/056708 | 5/2009 |

OTHER PUBLICATIONS

Nakagawa, S. et al. 1994. Appl. and Environ. Microbiol. 60: 3499-3502.*

* cited by examiner

*Primary Examiner* — Hamid R Badr
(74) *Attorney, Agent, or Firm* — Vedder Price P.C.; Thomas J. Kowalski; Deborah L. Lu

(57) ABSTRACT

The present invention relates to *Saccharomyces cerevisiae* strains suitable for the production of baker's yeasts which are osmotolerant and which exhibit intrinsic resistance to weak organic acids.

The strains of the present invention are obtained by means of a process of hybridization or of mutation of the industrial *S. cerevisiae* strain deposited on Jul. 8, 2010 with the CNCM [French National Collection of Microorganism Cultures] under number I-4341, or from an industrial strain related thereto via the Ty profile thereof and/or via quantitative trait locus mapping (QTL mapping).

19 Claims, No Drawings

SACCHAROMYCES CEREVISIAE STRAINS SUITABLE FOR THE PRODUCTION OF BAKER'S YEASTS WHICH ARE OSMOTOLERANT AND WHICH EXHIBIT INTRINSIC RESISTANCE TO WEAK ORGANIC ACIDS, METHODS FOR THE PREPARATION THEREOF AND USES

CROSS-REFERENCE TO RELATED APPLICATIONS

This application is a continuation-in-part of International Patent Application No. PCT/FR2011/051550, filed Jul. 1, 2011, published as WO 2012/110711, which in turn claims priority of French application FR 11 51354, filed on Feb. 18, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the field of *Saccharomyces cerevisiae* strains capable of producing baker's yeasts, for the methods for the preparation thereof, to the baker's yeasts produced from these strains, to the baker's dough(s) containing them and also to the breadmaking methods and bread products which can be obtained using these doughs. More especially, the present invention relates, in its most general aspect, to "industrial" *Saccharomyces cerevisiae* strains capable of producing baker's yeasts which are osmotolerant and which exhibit intrinsic resistance to weak organic acids.

BACKGROUND

Document WO 96/38538 teaches yeasts derived from improved *S. cerevisiae* strains which exhibit increased osmotolerance in that they give off gases (production of $CO_2$) advantageous in loaf doughs containing high concentrations of sugar from 16% to 25% (baker's percentages). This document is silent as to the behavior of these yeasts in the presence of mold inhibitors, such as weak organic acids.

Document U.S. Pat. No. 4,318,991 discloses a process for the production of baker's yeasts which have a high fermentative activity in a baker's dough even in the presence of mold-inhibiting agents, such as weak organic acids, for instance acetic acid or propionic acid. This process comprises a step of adding such an acid, in particular during the multiplication of the yeast, in the final stage of its propagation so as to "adapt" the yeast to said acid, in particular present in the form of calcium propionate (hereinafter denoted Calpro or else cpp) in baker's doughs. That document does not specify the behavior of the yeasts thus produced in doughs with a high sugar content.

A document, in the name of the applicant, U.S. Pat. No. 4,346,115 describes a process for preparing a baker's yeast made resistant to weak organic acids, from an osmotolerant strain, by discontinuous addition of molasses during the final cycle of its multiplication.

Another document, also in the name of the applicant, EP 1559322, teaches strains for producing, after adaptation to weak acids, yeasts which are even more effective, according to tests well known to those skilled in the art, and a control strain which has been the reference for about twenty years for obtaining commercial yeasts that are effective on sweet doughs in the presence of mold inhibitors.

In addition to the fact that the adaptation, mentioned above, to weak acids, in the form of calcium propionate for example, during the multiplication of the yeast, has certain costs, the latter can also have a negative impact on the fermentative activity of the yeast, in particular in the presence of sweet or highly sweet doughs.

The unfavorable common point of these prior art techniques aimed at improving the resistance of baker's yeasts to mold-inhibiting weak acids in sweet or non-sweet baker's doughs, by adapting the strains from which they are derived to said weak acids, is that they confer on the yeasts only a provisional/transient and non-permanent resistance to weak acids. The adaptation consists in exposing the yeast cells to a sublethal amount of a weak acid during their growth phase; this prior exposure subsequently enables the adapted cells to tolerate the presence of the same weak acid better when they are placed under fermentation conditions. In certain cases, a given weak acid can confer an adaptation with respect to the subsequent presence of another weak acid in the fermentation phase. These notions are exemplified in the article by Ferreira et al. (1997) International Journal of Food Microbiology 36, 145-153. The mechanisms of the adaptation to weak acids have been the subject of several studies. Some of these studies have been collated in the review article by Piper et al. (2001) Microbiology 147, 2635-2642. It is learnt therein that the adaptation is based on cell mechanisms involving several proteins, including certain membrane pumps. These mechanisms are non-genetic and essentially transient: they are set up by the cells as a reaction to the stress represented by the weak acid, but end up disappearing in the absence of this stress: the cells previously adapted return to the nonadapted cell state.

Other, much more complex, processes, such as those described in documents EP 645094 or WO 99/51746, teach a genetic modification of strains capable of producing baker's yeasts so as to make them intrinsically resistant to weak acids.

The applicant, continuing its studies to search for strains which are more effective still, has noted that a particular strain derived from its internal collection of osmotolerant strains has a genetic inheritance such that, if it is hybridized or mutated, according to conventional processes moreover, this provides a strain capable of producing a baker's yeast which is particularly effective and which, entirely surprisingly, does not require any adaptation before it is introduced into highly sweet doughs containing a weak acid in the form of calcium propionate (denoted Calpro, or cpp), for example.

It is this discovery which forms the basis of the present invention.

SUMMARY OF THE INVENTION

Thus, in its most general aspect, the present invention relates to a process for preparing an *S. cerevisiae* strain capable of producing a baker's yeast which exhibits osmotolerance and an intrinsic resistance to weak organic acids, from an industrial strain of *S. cerevisiae* deposited on Jul. 8, 2010 with the CNCM (Collection Nationale de Cultures de Microorganismes [French National Collection of Microorganism Cultures], Institut Curie, 25 rue du docteur Roux, 75724 Paris Cedex 15) under number I-4341, or from an industrial strain related thereto via the Ty profile thereof and/or via quantitative trait locus mapping (QTL mapping).

To the applicant's knowledge, this is the first time that a process for producing baker's yeast is taught which confers on said yeast both osmotolerance and an intrinsic resistance to weak acids while dispensing with the expensive and/or complex processes of the prior art.

In a first variant of the process according to the present invention, the preparation process comprises a step of hybridization of said industrial strain and at least one step of selection of the hybrid obtained, chosen from the group consisting of:

(i) a fermentative activity, measured with a Burrows and Harrison fermentometer in at least test A5' or tests A5 and A5', the hybrid selected being such that its gas release is at least 10%, preferably at least 15% to 25%, greater than that of a control strain consisting of the *S. cerevisiae* strain deposited on Jul. 8, 2010 with the CNCM [French National Collection of Microorganism Cultures] under number I-4341; (ii) a proof time in a No-Time Dough scheme on dough containing 18% of sugar (baker's percentages) in the presence of 0.4% of calcium propionate, the selected hybrids being capable of producing baker's yeasts by multiplication, in the absence of adaptation to calcium propionate, which give a proof time of between 85% and 105% and preferably between 95% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain; (iii) a proof time in a No-Time Dough scheme on dough containing 23% of sugar (baker's percentages) in the presence of 0.4% of calcium propionate, the hybrids selected being capable of producing baker's yeasts by multiplication, in the absence of adaptation to calcium propionate, which give a proof time of between 85% and 105% and preferably between 95% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain;

(iv) a proof time in a No-Time Dough scheme on dough containing 25% of sugar (baker's percentages), the hybrids selected being capable of producing baker's yeasts by multiplication, in the absence of adaptation to calcium propionate, which give a proof time of between 85% and 105% and preferably between 95% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain.

The present invention also relates to the following hybrids derived from the I-4341 strain:

the *Saccharomyces cerevisiae* strain deposited on May 11, 2010 with the CNCM [French National Collection of Microorganism Cultures] under number I-4312
and
the *Saccharomyces cerevisiae* strain deposited on May 11, 2010 with the CNCM [French National Collection of Microorganism Cultures] under number I-4313.

According to the second variant of the process of the present invention, the process comprises a step of mutagenesis of the industrial strain of *S. cerevisiae* deposited on Jul. 8, 2010 with the CNCM [French National Collection of Microorganism Cultures] under number I-4341, or of a strain related thereto via the Ty profile thereof and/or via quantitative trait locus mapping (QTL mapping) and at least one step of selection of the mutant obtained, chosen from the group consisting of:

(i) a fermentative activity, measured with a Burrows and Harrison fermentometer in test A5'; the mutant selected being such that its gas release is at least 5% to 20% greater than that of a control strain consisting of the industrial strain of *S. cerevisiae* deposited on Jul. 8, 2010 with the CNCM [French National Collection of Microorganism Cultures] under number I-4341;

(ii) a proof time in a No-Time Dough scheme on dough containing 15% of sugar (baker's percentages) in the presence of 0.4% of calcium propionate, the mutant selected being capable of producing baker's yeasts by multiplication, in the absence of adaptation to calcium propionate, which give a proof time of between 95% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain;

(iii) a proof time in a No-Time Dough scheme on dough containing 18% of sugar (bakers' percentages) in the presence of 0.4% of calcium propionate, the mutant selected being capable of producing baker's yeasts by multiplication, in the absence of adaptation to calcium propionate, which give a proof time of between 90% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain;

(iv) a proof time in a No-Time Dough scheme on dough containing 23% of sugar (baker's percentages) in the presence of 0.4% of calcium propionate, the mutant selected being capable of producing baker's yeasts by multiplication, in the absence of adaptation to calcium propionate, which give a proof time of between 90% and 105% of the proof time given by a control baker's yeast produced from the industrial strain of *S. cerevisiae* deposited on Jul. 8, 2010 with the CNCM [French National Collection of Microorganism Cultures] under number I-4341 by multiplication with adaptation to the presence of calcium propionate of said strain.

The subject of the present invention is also the *Saccharomyces cerevisiae* strains deposited on Dec. 8, 2010 with the CNCM [French National Collection of Microorganism Cultures] under numbers I-4409 and I-4410.

The subject of the present invention is also a baker's yeast which can be obtained by multiplication, without adaptation to the presence of weak acid(s), of a strain according to the present invention, or obtained by means of a process in accordance with the present invention.

The applicant has noted that, when said baker's yeasts are produced with adaptation, the benefit in terms of reduction of the proof time is amplified.

The subjects of the present invention are, in addition:
a baker's dough containing a baker's yeast as claimed in the present invention;
said baker's dough preferably being chosen from doughs in which the fermentation is carried out both in the presence of an osmotic pressure due to the presence of at least 15% of sugar, preferably at least 18% of sugar, more preferably at least 23% of sugar and more preferably at least 25% of sugar (baker's percentages) and in the presence of a mold inhibitor of weak organic acid type, preferably in the form of calcium propionate.

The subject of the present invention is also a process for preparing a baked bread product by using said baker's dough.

The subject of the present invention is also a bread product which can be obtained by means of said preparation process.

Other characteristics and advantages will now be described in greater detail by means of exemplary embodiments of the invention, which are given purely by way of illustration and are nonlimiting.

DETAILED DESCRIPTION

In the present invention, the term "osmotolerant baker's yeast" is intended to mean a yeast which has at least one of the following properties:
  invertase activity of less than 35 units, preferably less than 30 and even more preferably less than 20, the invertase unit being defined as the production of one micromol of reducing sugars in 5 min per mg of yeast dry matter at 30° C. and at a pH of 4.7 without plasmolysis of the yeast, namely half a micromol of inverted sucrose (test specified in U.S. Pat. No. 4,318,929);
  passes at least one of the following tests with a Burrows and Harrison fermentometer described in "Journal of Institute of Brewing", vol. LXV, No. 1, January-February 1959 and which are defined in patent EP 1559322 as A5, A5', A6 and A6';
  passes at least one of the following breadmaking tests in comparison with the adapted I-4341 strain and always in the presence, in the baker's dough, of 0.4% calcium propionate and of high sugar contents, said tests being called, in the present invention, NT15%+, NT18%+, NT23%+, NT25%+: they correspond to measurements of the proof time in "No-Time Dough" schemes, namely direct processes in which there is virtually no first fermentation between intensive kneading and the division of the dough, the dough pieces obtained being fermented in molds between 35° C. and 40° C. The latter fermentation, which is the essential fermentation in such a process, is called "proof". The proof time is defined as the time required for a baker's dough to reach a given height in the mold, corresponding to the desired development of the dough in order for it to be placed in the oven.

Preferably, an osmotolerant yeast according to the invention has at least two of the properties as defined in the above-mentioned tests.

In the present invention, the expression "intrinsic resistance of a yeast to weak organic acids, present for example in the form of calcium propionate," is intended to mean a resistance which is neither induced, by adaptation for example, nor acquired after genetic modification of said yeast other than by hybridization or mutation of the strain from which it is derived and as taught below.

In the present invention, the term "industrial strain" is intended to mean a strain which, unlike "laboratory" strains, is not necessarily haploid or diploid, but the ploidy of which is often more complex.

In the present invention, the term "Ty profile" of a strain is intended to mean any profile obtained by PCR using primers directed against target sequences corresponding to genetic "scars" resulting from movements of transposons (Ty). Approximately 100 copies of these sequences are present in the *Saccharomyces cerevisiae* genome, more particularly in the sequences close to the genes encoding the tRNAs. The number and the distribution on the genome of the Ty elements are variable from one strain to another and make it possible to demonstrate a considerable polymorphism between strains. This technique is now described in standard DIN CEN/TS 15790 (March 2009) for the identification of probiotic yeasts for animal feeding stuffs.

In the present invention, the expression "quantitative trait locus mapping (QTL mapping)" is intended to mean a technique which consists of the construction of genetic maps which make it possible to locate loci (regions of the chromosome) involved in the variation of quantitative traits linked to more easily identifiable loci, markers.

In the context of the present invention, all the percentages mentioned in the selection tests, unless otherwise mentioned, are given as "baker's" percentages, which are well known to those skilled in the art; these percentages represent percentages by weight of the ingredients (for example, sugars, calcium propionate, etc.) present relative to the weight of the flour representing 100%.

Although the present invention and its advantages have been described in detail, it should be understood that various changes, substitutions and alterations can be made herein without departing from the spirit and scope of the invention as defined in the appended claims. The present invention will be further illustrated in the following Examples which are given for illustration purposes only and are not intended to limit the invention in any way.

EXAMPLES

Example 1

Preparation of the Hybrids

The I-4312 and I-4313 hybrid strains, which are subjects of the present invention, are produced by systematic crossings between one another of strains of the applicant's internal collection, chosen as being osmotolerant and/or osmotolerant and not very sensitive to the presence of weak organic acids or salts thereof, used as mold inhibitors, such as those deposited with the Collection Nationale de Culture de Microorganismes [French National Collection of Microorganism Cultures] of the Institut Pasteur, 25 rue du Docteur Roux, 75724 Paris Cedex 15, France, on Jul. 8, 2010 under number I-4341 and on Feb. 9, 2011 under No. I-4448.

The hybridization program is carried out according to conventional techniques such as those described in the "Techniques and Protocols" chapters 21 to 23 of the manual "Methods in Yeast Genetics, A Cold Spring Harbor Laboratory Course Manual, 2000 Edition" by D. Burke, D. Dawson and T. Stearns, Cold Spring Harbor Laboratory Press (ISBN 0-87969-588-9).

Example 2

Preparation of the Yeasts in Accordance with the Invention From the Hybrids of Example 1

To produce the baker's yeasts according to the invention, the hybrid strains as obtained in example 1 are placed in culture in flasks or in fermenters in the media which are known, but free of weak acid.

In flasks, use may be made of the YPD culture medium as described in appendix A devoted to culture media of the manual "Methods in Yeast Genetics, A Cold Spring Harbor Laboratory Course Manual, 2000 Edition" by D. Burke, D. Dawson and T. Stearns, Cold Spring Harbor Laboratory Press (ISBN 0 87969-588-9).

In fermenters, conventionally, the culture conditions are such that the metabolism of the yeast strain is essentially respiratory and/or such that there is essentially no ethanol production.

The term "essentially" means that these conditions are confirmed over the total duration of the culture, but that it is possible that, from time to time, these conditions are not confirmed in fed-batch mode, for example during the first hours of the culture which are equivalent to a duration of between ¼ to ⅓ of the culture duration, and in particular for the first 5 hours of a culture in fed-batch mode.

The expression "the metabolism of the yeast strain is essentially respiratory" means that the carbon is oxidized, and not fermented, over the total duration of the culture, a part of the carbon possibly being transiently fermented.

The expression "there is essentially no ethanol production" means that the ethanol concentration at the end of culturing is less than 1%, preferably less than 0.1%, more preferentially less than 0.01% and more preferentially less than 0.001%.

Those skilled in the art know how to adjust the parameters for culturing a given yeast strain so that the culture conditions are such that the metabolism of said strain is essentially respiratory and/or such that there is essentially no ethanol production.

The yeast strain according to the invention is placed in the presence of the culture medium under aerobic conditions.

Preferably, the yeast strain according to the invention is placed in the presence of the culture medium in a fermenter suitable for the production of yeast. The volume of the fermenter can range from a few milliliters to several cubic meters.

The fermenter is also subsequently called a reactor.

The fermenter is preferably suitable for culturing under aerobic conditions.

The yeast strain is preferably placed in the presence of the culture medium in the context of culturing in fed-batch mode and/or in continuous mode.

The expression "culturing in fed-batch mode" or "fed-batch culturing" or "fed-batch mode" denotes herein culturing in a fermenter which is gradually fed with the culture medium, but from which no medium volume is withdrawn. In such a process, the culture volume is variable (and increasing) in the fermenter. The feed flow rate in culturing in fed-batch mode is constant or variable.

An example of fed-batch culturing is culturing carried out under the conditions described in reference book "Yeast Technology", 2nd edition, 1991, G. Reed and T. W. Nagodawithana, published by Van Nostrand Reinhold, ISBN 0 442-31892-8.

The culture medium comprises as constituents the mixture of sugar and the other elements required for the growth of the yeasts.

The other elements required for the growth of the yeasts are the following: at least one nitrogen source, at least one sulfur source, at least one phosphorus source, at least one source of vitamins and/or at least one source of minerals.

These other elements are provided in sufficient amounts so as not to constitute a factor limiting the growth of the yeasts.

The nitrogen source is, for example, provided in the form of ammonium sulfate, ammonium hydroxide, diammonium phosphate, ammonia, urea and/or a combination thereof The sulfur source is, for example, provided in the form of ammonium sulfate, magnesium sulfate, sulfuric acid and/or a combination thereof The phosphorus source is, for example, provided in the form of phosphoric acid, potassium phosphate, diammonium phosphate, monoammonium phosphate and/or a combination thereof The source of vitamins is, for example, provided in the form of molasses, yeast hydrolysate, a solution of pure vitamin or of a mixture of pure vitamins and/or a combination thereof The source of vitamins provides the yeast with all the vitamins in amounts which are at least equivalent to those recommended in the reference manuals. Several sources of vitamins can be combined.

The source of minerals is, for example, provided in the form of molasses, a mixture of mineral salts and/or a combination thereof The source of minerals provides the yeast with all of the macroelements and trace elements in amounts which are at least equivalent to those recommended in the reference manuals. Several sources of minerals can be combined.

One and the same substance can provide several different elements.

The conditions for in-fermenter production of the baker's yeast are explained in detail by A. Loiez in the chapter "Production of baker's yeast by biotechnology" of the Techniques de l'Ingénieur [Techniques for the Engineer], Reference J6013 of Mar. 10, 2003.

The same culture medium of the hybrids according to the invention is used for the I-4341 reference strain, to which they will be compared, but while carrying out, with regard to said reference strain, an additional "adaptation" step according to the technique described in patents U.S. Pat. No. 4,318,991 or U.S. Pat. No. 4,346,115 or according to the combined teaching of these two documents.

The process for preparing the baker's yeast comprises at least the first two steps of the set of the following steps consisting in:
 multiplying a pure strain under semi-aerobic and then aerobic conditions,
 separating, by centrifugation, the yeast thus produced from its culture medium, so as to provide a liquid "cream yeast" containing from 14% to 25% of dry matter, or more if the cream yeast is mixed with osmotic products,
 filtering the liquid cream yeast thus obtained, preferably on a rotary filter under vacuum, and providing a dehydrated fresh yeast containing from 26% to 35% of dry matter,
 mixing said yeast thus obtained, even in the form of fresh yeast cakes, or in the form of crumbled fresh yeast containing approximately 30% of dry matter, or else in the form of particles, preferably granules, if the yeast is intended to be dried,
 drying, in a sparing manner, in a stream of hot air, for example by fluidization, of the yeast particles obtained by extrusion,
 packaging before marketing.

Example 3

Comparison of the Effectiveness of the Non-Adapted Yeasts According to the Invention with the Adapted Control Strain Example 3.1

Presentation of the Tests 3.1.1. Fermentometer Tests

The tests are carried out using the Burrows and Harrison fermentometer described in the "Journal of Institute of Brewing", vol. LXV, No. 1, January-February 1959 and are defined in the following way:

Test A5

A yeast suspension is prepared in the following way:
1. 200 mg of dry matter of the yeast to be tested
2. 5 ml of a solution containing 108 g/l of NaCl and 16 g/l of $(NH4)2SO4$
3. Bring the volume to 20 ml with distilled water.

15 ml of the above suspension (i.e. 150 mg of yeast dry matter) are equilibrated at a temperature of 30° C. for 15 minutes. A mixture of 20 g of flour and 4 g of sucrose equilibrated beforehand overnight at 30° C. is added to this suspension. The whole mixture is homogenized for a period of 35 seconds.

The dough formed is incubated in a hermetically closed container placed at 30° C. The gas release (expressed in ml at 760 mmHg) is recorded over a total period of 120 minutes (this period can be adjusted).

Test A5'

Protocol identical to A5 except that:
1. 500 µl of a solution at 16% (w/v) of calcium propionate (calpro) are added on top of the flour+sugar mixture just before the 35-second mixing phase.

Test A5"

Protocol identical to A5 except that:
1. 1 ml of a solution at 16% (w/v) of calcium propionate is added on top of the flour+sugar mixture just before the 35-second mixing phase.

Test A6

Protocol identical to PS4g except that:
1. The yeast suspension is prepared with 400 mg of dry matter (instead of 200 mg), which leads to it being in an amount of 300 mg of yeast dry matter that is used in the test.
2. The flour+sugar mixture is composed of 25 g of flour (instead of 20 g) and 6.5 g of sucrose (instead of 4 g).

Tests A51 and A51' (With Calcium Propionate)

For Fresh Yeast

A yeast suspension is prepared in the following way:
1. 400 mg of dry matter of the yeast to be tested.
2. Mix with the volume of distilled water required to achieve a total volume of water of 6.8 ml while taking into account the water provided by the fresh yeast (typically 70% of the weight of a pressed yeast).
3. Equilibrate at 30° C. for 22 minutes.
4. Add 4.5 ml of a solution containing 73.6 g/kg of NaCl and homogenize.

20 g of flour and 3 g of sucrose are added to the above suspension. The whole is mixed for a period of 35 seconds.

The gas release (expressed in ml at 760 mmHg) is recorded over a total period of 120 minutes (this period can be adjusted). The measurement begins 36 minutes after the beginning of the protocol.

This protocol exists as a variant including the presence of calcium propionate. In this case, in step 4 of the preparation of the yeast suspension, the solution containing 73.6 g/kg of NaCl also contains 17.4 g/kg of calcium propionate.

For Dry Yeast

Mix 20 g of flour, 3 g of sucrose and 400 mg of dry matter of the yeast to be tested. Equilibrate at 30° C. for 12 minutes.

Add 6.8 ml of distilled water and 4.5 ml of a solution containing 73.6 g/kg of NaCl and homogenize for 35 seconds.

36 minutes after the addition of the distilled water, carry out a second homogenization identical to the first.

The gas release (expressed in ml at 760 mmHg) is recorded over a total period of 120 minutes (this period can be adjusted). The measurement begins 60 minutes after the beginning of the protocol.

Tests A61 and A61' (With Calcium Propionate)

For Fresh Yeast

A yeast suspension is prepared in the following way:
1. 700 mg of dry matter of the yeast to be tested.
2. Mix with the volume of distilled water required to achieve a total volume of water of 7.5 ml while taking into account the water provided by the fresh yeast (typically 70% of the weight of a pressed yeast).
3. Equilibrate at 30° C. for 22 minutes.
4. Add 5.75 ml of a solution containing 73.6 g/kg of NaCl and homogenize.

25 g of flour and 6.5 g of sucrose are added to the above suspension.

The whole is mixed for a period of 35 seconds.

The gas release (expressed in ml at 760 mmHg) is recorded over a total period of 120 minutes (this period can be adjusted). The measurement begins 36 minutes after the beginning of the protocol.

This protocol exists as a variant including the presence of calcium propionate. In this case, in step 4 of the preparation of the yeast suspension, the solution containing 73.6 g/kg of NaCl also contains 17.4 g/kg of calcium propionate.

For Dry Yeast

Mix 25 g of flour, 6.5 g of sucrose and 700 mg of dry matter of the yeast to be tested. Equilibrate at 30° C. for 12 minutes.

Add 7.5 ml of distilled water and 5.75 ml of a solution containing 73.6 g/kg of NaCl and homogenize for 35 seconds.

36 minutes after the addition of the distilled water, carry out a second homogenization identical to the first.

The gas release (expressed in ml at 760 mmHg) is recorded over a total period of 120 minutes (this period can be adjusted). The measurement begins 60 minutes after the beginning of the protocol.

3.1.2. Breadmaking Tests, 4 Recipes Are Tested:

recipe PT1 containing 15% by weight (baker's percentage) of sucrose and 0.4% by weight (baker's percentage) of calcium propionate;

recipe PT2 containing 18% by weight (baker's percentage) of sucrose and 0.4% by weight (baker's percentage) of calcium propionate;

recipe PT3 containing 23% by weight (baker's percentage) of sucrose and 0.4% by weight (baker's percentage) of calcium propionate;

recipe PT4 containing 25% by weight (baker's percentage) of sucrose and 0.4% by weight (baker's percentage) of calcium propionate.

In tests 1 to 4, the difference in proof time between, on the one hand, a dry yeast obtained with the strain to be evaluated and, on the other hand, a dry yeast obtained with a control strain "C" is measured in a given breadmaking process and with the given recipes. The effectiveness is measured as percentage difference between the strain tested and the control strain. A negative difference corresponds to a greater effectiveness than that of the control strain.

The recipes used in the tests and expressed in baker's percentages are given in the following table. This table also includes the details of the various protocols used.

|  | No Time 15%+ | No Time 18%+ | Rotimani 23%+ | No Time 25%+ |
|---|---|---|---|---|
|  | TEST | | | |
|  | PT1 Recipe 1 | PT2 Recipe 2 | PT3 Recipe 3 | PT4 Recipe 4 |
| FORMULAE | | | | |
| Flour | 100% | 100% | 100% | 100% |
| Water | 54% | 52% | 45% | 50% |
| Sucrose | 15% | 18% | 23% | 25% |
| Salt | 1.7% | 1% | 1.5% | 1.7% |
| Dry yeast | 1.5% | 1% | 2.3% | 2% |
| Fat | 7.5% | 5% | 10% | 7.5% |
| Improver | — 1% | 0.5% | 0.3% | — 1% |
| Milk powder | — | 4% | 3% | — |
| Eggs | — | 6% | 10% | — |
| Calpro | 0.4% | 0.4% | 0.3% | 0.4% |
| TEMPERATURES | | | | |
| Premises + flour + water | 64° C. | 70° C. | 70° C. | 64° C. |
| Waterbath Kneading machine | 22.5° C. | 23.5° C. | 24.5° C. | 22.5° C. |
| Dough | 27° C. | 28° C. | 29° C. | 27° C. |
| DIAGRAM | | | | |
| Kneading Mac Duffy | L5 R5 H4 | L1 + MG1 L1 H4 | L1 + MG1 L1 H5.5 | L5 R5 H4 |
| Bulk Fermentation | 10 min | 15 min | 10 min | 10 min |
| Division | 320 g | 320 g | 320 g | 320 g |
| Rounding - slackening | | | | |
| Time from end kneading - beginning shaping | 25 min | 50 min | 25 min | 25 min |
| Shaping | Shaping machine US | | | |
| Proofing Forma Oven | 35° C. 90% RH | 35° C. 90% RH | 35° C. 90% RH | 35° C. 90% RH |
| Baking Reed Oven | 21 min 190° C. | 21 min 190° C. | 21 min 190° C. | 21 min 190° C. |

Details of the Procedure:

The test protocol applied to the various recipes above in tests PT1 to PT4 is the following:
1. Weigh out the various ingredients.
2. Measure the ambient temperature and the temperature of the flour.
3. Adjust the temperature of the water so as to obtain a dough temperature, at +/−0.5° C., of 27° C. for recipes 1 and 4; 28° C. for recipe 2 and 29° C. for recipe 3.
4. Place the ingredients in a Mac Duffy® bowl of a Hobart A200® kneading machine, the jacket of which is thermostated beforehand with water at 22.5° C. (recipes 1 and 4) or 23.5° C. (recipe 2) or 24.5° C. (recipe 3).
5. Mix the dry ingredients at first speed for 1 minute.
6. The kneading diagram depends on the recipe used:
recipes 1 and 4:
the fat is incorporated after the dry premixing
the pouring water is added
blending is carried out for 5 minutes at first speed (L5)
the resulting product is left to stand for 5 minutes (R5)
kneading is carried out for 4 minutes at second speed (H4)
recipe 2:
the pouring water is added after the dry premixing
blending is carried out for 1 minute at first speed (L1)
the resulting product is left to stand for 1 minute for the addition of the fat (+MG1)
blending is carried out for 1 minute at first speed (L1)
kneading is carried out for 4 minutes at second speed (H4)
recipe 3:
the pouring water is added after the dry premixing
blending is carried out for 1 minute at first speed (L1)
the resulting product is left to stand for 1 minute for the addition of the fat (+MG1)
blending is carried out for 1 minute at first speed (L1)
kneading is carried out for 5 minutes 30 seconds, at second speed (H5.5).
7. Verify the temperature of the dough obtained at the end of kneading.
8. Bulk fermentation at 23° C. for 10 minutes (recipes 1, 3 and 4) or 15 minutes (recipe 2)
9. Divide into 320 g pieces.
10. Loose round and cover.
11. Leave to stand for 10 minutes (recipes 1, 3 and 4) or 30 minutes (recipe 2).
12. Shape the dough.
13. Place the 320 g dough pieces into pans (dimensions: base of pan 185×75 mm; top of pan 200×90 mm; pan height 75 mm).
14. Determine the proof time, in a Stéricult® incubator at 35° C. and 90% relative humidity. The proof time is the time elapsed between placement of the pans in the incubator and the moment at which the dough reaches a height of 85 mm in the pan.
15. Bake in a Reed® tray oven for 21 minutes at 190° C.

Example 3.2

Results

TABLE 1

Fermentometer tests: differences between hybrid according to the invention and I-4341 parent

| | Biomass produced in a flask, evaluation on fresh yeast | | | |
|---|---|---|---|---|
| Test | Parent 1 I-4341 without adaptation | Parent 2 I-4448 without adaptation | I-4312 without adaptation | I-4313 without adaptation |
| A5 | 122 | 120 | 137 | 132 |
| A5' | 92 | 98 | 114 | 115 |
| Gain/parents | | | 17 & 24% | 18 & 24% |
| Test | I-4341 without adaptation | I-4341 with adaptation | I-4312 without adaptation | I-4313 without adaptation |
| | Biomass produced in a 7 L fermenter, evaluation on fresh yeast | | | |
| A5 | 96 | 99 | 121 | 126 |
| A5' | 79 | 108 | 114 | 107 |
| A61 | 139 | 179 | 209 | 225 |
| A61' | 88 | 105 | 121 | 131 |
| | Biomass produced in a 20 L fermenter, evaluation on dry yeast | | | |
| A5 | 102 | 105 | 105 | 97 |
| A5' | 99 | 107 | 90 | 80 |
| A51 | 159 | 214 | 173 | 209 |
| A51' | 124 | 160 | 107 | 134 |
| A61 | 167 | 232 | 169 | 241 |
| A61' | 95 | 114 | 97 | 125 |

TABLE 2

No-Time Dough scheme test, hybrid according to the invention vs. the yeast obtained from the non-adapted strain deposited on Jul. 8, 2010 with the CNCM [French National Collection of Microorganism Cultures] under No. I-4342.
Biomass produced in a 20 L fermenter, evaluation on dry yeast

| Test | I-4342 without adaptation | I-4313 without adaptation |
|---|---|---|
| PT1 | T | −14% |
| PT2 | T | −9% |
| PT3 | T | −17% |

TABLE 3

No-Time Dough scheme, hybrids according to the invention vs. adapted control (= adapted I-4341)
Biomass produced in a 20 L fermenter, evaluation on dry yeast

| Test | I-4341 with adaptation | I-4313 without adaptation |
|---|---|---|
| PT2 | T | 1% |
| PT3 | T | −5% |
| PT4 | T | 3% |

Conclusion: The non-adapted yeasts according to the invention behave substantially identically or even better compared with an adapted control yeast, produced by crossing of one of the best osmotolerant strains available in the applicant's internal collection and deposited under number I-4341 and of a commercial strain not very sensitive to weak acids.

These results are surprising since it was absolutely not foreseeable to accumulate the preexisting advantages of the two parents by hybridizing industrial strains, especially while exceeding by 15% to 25% the gas release values of their two parents.

The present invention thus provides hybrids capable of producing baker's yeasts at a lower cost while at the same time being as effective in highly sweet baker's doughs and in the presence of mold inhibitors such as calcium propionate.

Example 4

Preparation of the I-4409 and I-4410 Mutants

The I-4341 strain was subjected to mutagenesis by exposure to ultraviolet radiation. A population of mutants was evaluated in tests A5 and A5' after production in flasks. The I-4409 and I-4410 strains were initially selected from this population.

Example 5

Preparation of the Yeast From the Mutants of Example 4 (Idem Example 2)

Example 6

Comparison of the Effectiveness With a Control Yeast

Biomass produced in a flask, evaluation on fresh yeast

| Test | I-4341 without adaptation | I-4409 without adaptation | I-4410 without adaptation |
|---|---|---|---|
| A5 | 121 | 117 | 126 |
| A5" | 88 | 105 | 96 |
| Gain/I-4341 in A5" (%) | | 19 | 9 |

Biomass produced in a 20 L fermenter, evaluation on dry yeast

| Test | I-4341 with adaptation | I-4409 without adaptation | Difference (%) |
|---|---|---|---|
| A5 | 101 | 101 | 0 |
| A5' | 104 | 100 | −4 |
| A51 | 104 | 114 | 10 |
| A51' | 136 | 159 | 17 |

| Test | I-4341 with adaptation | I-4410 without adaptation | Difference (%) |
|---|---|---|---|
| A5 | 96 | 106 | 10 |
| A5' | 101 | 97 | −4 |

The breadmaking results obtained with these yeasts are below (tests PT2 and PT3)

| Test | I-4341 with adaptation | I-4410 without adaptation | I-4410 with adaptation |
|---|---|---|---|
| PT2 | T | 2% | −11% |
| PT3 | T | 2% | −4% |

| Test | I-434 with adaptation | I-4409 without adaptation |
|---|---|---|
| PT1 | T | 3% |
| PT2 | T | 5% |
| PT3 | T | −1% |

The invention will be further described by the following numbered paragraphs:

1. A *Saccharomyces cerevisiae* strain obtained by means of a hybridization process or mutation process of the industrial stain of *Saccharomyces cerevisiae* deposited on Jul. 8, 2010 with the CNCM under No. I-4341, or from an industrial strain related thereto via its Ty profile and/or via quantitative trait locus mapping (QTL mapping), wherein said *Saccharomyces* cerevisiae strain produces a baker's yeast which exhibits osmotolerance and an intrinsic resistance to weak organic acids.

2. The *Saccharomyces cerevisiae* strain according to paragraph 1, wherein the hybridization process comprises a step of hybridization of the industrial strain with the strain deposited on Feb. 9, 2011 with the CNCM under No. I-4448 and at least one step of selection of the hybrid obtained, wherein the step of selection is selected from the group consisting of i. measuring a fermentative activity using a Burrows and Harrison fermentometer in at least one of tests A5' and A6', wherein the hybrid selected is such that its gas release is at least 10% than that of a control strain consisting of the *Saccharomyces cerevisiae* strain deposited on Jul. 8, 2010 with the CNCM under No. I-4341, ii. measuring a proof time in a No-Time Dough scheme on dough containing, in baker's percentages, 15%, 18%, 23% or 25% of sugar in the presence of 0.4% of calcium propionate, wherein the hybrids selected produce baker's yeasts by multiplication in the absence of adaptation to calcium propionate, which give a proof time of between 85% and 105% of the proof time given by a control baker's yeast produced from the industrial strain of *Saccharomyces cerevisiae* deposited on Jul. 8, 2010 with the CNCM under I-4341 by multiplication with adaptation to the presence of calcium propionate of said strain.

3. The *Saccharomyces cerevisiae* strain according to paragraph 2, wherein said strain was deposited on May 11, 2010 with the CNCM under No. I-4312.

4. The *Saccharomyces cerevisiae* strain according to paragraph 2, wherein said strain was deposited on May 11, 2010 with the CNCM under No. I-4313.

5. The *Saccharomyces cerevisiae* strain according to paragraph 1, wherein the mutation process comprises a step of mutagenesis of the industrial strain and at least one step of selection of the mutant obtained, wherein the step of selection is selected from the group consisting of:

i. measuring a fermentative activity using a Burrows and Harrison fermentometer in test A5", wherein the mutant selected is such that its gas release is from 5% to 20% greater than that of a control strain consisting of the *Saccharomyces cerevisiae* strain deposited on Jul. 8, 2010 with the CNCM under No. I-4341, ii. measuring a proof time in a No-Time Dough scheme on dough containing, in baker's percentages, 15%, 18% or 23% of sugar in the presence of 0.4% of calcium propionate, wherein the mutant selected produces baker's yeasts by multiplication in the absence of adaptation to calcium propionate, which give a proof time of between 90% and 105% of the proof time given by a control baker's yeast produced from the *Saccharomyces cerevisiae* strain deposited on Jul. 8, 2010 with the CNCM under I-4341 by multiplication with adaptation to the presence of calcium propionate of said strain.

6. The *Saccharomyces cerevisiae* strain according to paragraph 5, wherein said strain was deposited with the CNCM under No. I-4409.

7. The *Saccharomyces cerevisiae* strain according to paragraph 5, wherein said strain was deposited with the CNCM under No. I-4410.

8. A baker's yeast obtained by multiplication, without adaptation to the presence of weak acid(s), of a strain obtained by means of a the process according to paragraph 1.

9. A baker's yeast which can be obtained by multiplication, with adaptation to the presence of weak acid(s), of a strain obtained by means of the process according to paragraph 1.

10. A baker's dough comprising a baker's yeast according to paragraph 8.

11. A baker's dough comprising a baker's yeast according to paragraph 9.

12. The baker's dough according to paragraph 10 or paragraph 11 wherein said dough is selected from doughs in which the fermentation is carried out both in the presence of a mold inhibitor of weak organic acid type and in the presence of an osmotic pressure due to the presence of at least 15% of sugar or at least 18% of sugar or at least 23% of sugar, wherein the percentages are baker's percentages.

13. The baker's dough according to paragraph 12, wherein the mold inhibitor is calcium propionate.

14. A process for preparing a baked bread product comprising a step of using a baker's dough according to paragraph 10.

15. A process for preparing a baked bread product comprising a step of using a baker's dough according to paragraph 11.

16. A bread product obtained by the process according to paragraph 14 or paragraph 15.

It is to be understood that the invention is not limited to the particular embodiments of the invention described above, as variations of the particular embodiments may be made and still fall within the scope of the appended claims.

The invention claimed is:

1. A *Saccharomyces cerevisiae* strain obtained by means of a hybridization process comprising the hybridization of the industrial *Saccharomyces cerevisiae* strain No. I-4341 with *Saccharomyces cerevisiae* strain No. I-4448 or by means of a random mutation process of the industrial *Saccharomyces cerevisiae* strain No. I-4341, wherein said *Saccharomyces cerevisiae* strain produces, by multiplication in the absence of adaptation to the presence of weak acid(s), a baker's yeast which exhibits osmotolerance and an intrinsic resistance to weak organic acids.

2. The *Saccharomyces cerevisiae* strain according to claim 1, wherein the hybridization process further comprises at least one step of selection of the hybrid obtained, wherein the step of selection is selected from the group consisting of:

i. measuring a fermentative activity using a Burrows and Harrison fermentometer in at least one of tests A5' and A6', wherein the hybrid selected is such that its gas release is at least 10% greater than that of a control strain consisting of the *Saccharomyces cerevisiae* strain No. I-4341, ii. measuring a proof time in a No-Time Dough scheme on dough containing, in baker's percentages, 15%, 18%, 23% or 25% of sugar in the presence of 0.4% of calcium propionate, wherein the hybrids selected produce baker's yeasts by multiplication in the absence of adaptation to calcium propionate, which give a proof time of between 85% and 105% of the proof time given by a control baker's yeast produced from the industrial *Saccharomyces cerevisiae* strain No. I-4341 by multiplication with adaptation to the presence of calcium propionate of said strain.

3. The *Saccharomyces cerevisiae* strain according to claim 2, wherein said strain is *Saccharomyces cerevisiae* strain No. I-4312.

4. The *Saccharomyces cerevisiae* strain according to claim 2, wherein said strain is *Saccharomyces cerevisiae* strain No. I-4313.

5. The *Saccharomyces cerevisiae* strain according to claim 1, wherein the random mutation process comprises a step of mutagenesis of the industrial strain and at least one step of selection of the mutant obtained, wherein the step of selection is selected from the group consisting of:

i. measuring a fermentative activity using a Burrows and Harrison fermentometer in test A5', wherein the mutant selected is such that its gas release is from 5% to 20% greater than that of a control strain consisting of the *Saccharomyces cerevisiae* strain No. I-4341, ii. measuring a proof time in a No-Time Dough scheme on dough containing, in baker's percentages, 15%, 18% or 23% of sugar in the presence of 0.4% of calcium propionate, wherein the mutant selected produces baker's yeasts by multiplication in the absence of adaptation to calcium propionate, which give a proof time of between 90% and 105% of the proof time given by a control baker's yeast produced from the *Saccharomyces cerevisiae* strain No. I-4341 by multiplication with adaptation to the presence of calcium propionate of said strain.

6. The *Saccharomyces cerevisiae* strain according to claim 5, wherein said strain is *Saccharomyces cerevisiae* strain No. I-4409.

7. The *Saccharomyces cerevisiae* strain according to claim 5, wherein said strain is *Saccharomyces cerevisiae* strain No. I-4410.

8. A baker's yeast obtained by multiplication, without adaptation to the presence of weak acid(s), of a strain obtained by means of the process according to claim 1.

9. A baker's yeast which can be obtained by multiplication, with adaptation to the presence of weak acid(s), of a strain obtained by means of the process according to claim 1.

10. A baker's dough comprising a baker's yeast according to claim 8.

11. A baker's dough comprising a baker's yeast according to claim 9.

12. The baker's dough according to claim 10, wherein said dough is selected from doughs in which the fermentation is carried out both in the presence of a mold inhibitor of weak organic acid type and in the presence of an osmotic pressure due to the presence of at least 15% of sugar or at least 18% of sugar or at least 23% of sugar, wherein the percentages are baker's percentages.

13. The baker's dough according to claim 12, wherein the mold inhibitor is calcium propionate.

14. A process for preparing a baked bread product comprising a step of using a baker's dough according to claim 10.

15. A process for preparing a baked bread product comprising a step of using a baker's dough according to claim 11.

16. A bread product obtained by the process according to claim 14.

17. A method for obtaining a *Saccharomyces cerevisiae* strain which produces, by multiplication in the absence of adaptation to the presence of weak acid(s), a baker's yeast which exhibits osmotolerance and an intrinsic resistance to weak organic acids, said method comprising a hybridization process comprising the hybridization of the industrial *Saccharomyces cerevisiae* strain No. I-4341 with the *Saccharomyces cerevisiae* strain No. I-4448 or a random mutation process of the industrial *Saccharomyces cerevisiae* strain No. I-4341.

18. The method according to claim 17, wherein the hybridization process further comprises at least one step of selection of the hybrid obtained, wherein the step of selection is selected from the group consisting of:

i. measuring a fermentative activity using a Burrows and Harrison fermentometer in at least one of tests A5' and A6', wherein the hybrid selected is such that its gas release is at least 10% greater than that of a control strain consisting of the *Saccharomyces cerevisiae* strain No. I-4341, ii. measuring a proof time in a No-Time Dough scheme on dough containing, in baker's percentages, 15%, 18%, 23% or 25% of sugar in the presence of 0.4% of calcium propionate, wherein the hybrids selected produce baker's yeasts by multiplication in the absence of adaptation to calcium propionate, which give a proof time of between 85% and 105% of the proof time given by a control baker's yeast produced from the industrial *Saccharomyces cerevisiae* strain No. I-4341 by multiplication with adaptation to the presence of calcium propionate of said strain.

19. The method according to claim 17, wherein the random mutation process comprises a step of mutagenesis of the industrial strain and at least one step of selection of the mutant obtained, wherein the step of selection is selected from the group consisting of:

i. measuring a fermentative activity using a Burrows and Harrison fermentometer in test A5', wherein the mutant selected is such that its gas release is from 5% to 20% greater than that of a control strain consisting of the *Saccharomyces cerevisiae* strain No. I-4341, ii. measuring a proof time in a No-Time Dough scheme on dough containing, in baker's percentages, 15%, 18% or 23% of sugar in the presence of 0.4% of calcium propionate, wherein the mutant selected produces baker's yeasts by multiplication in the absence of adaptation to calcium propionate, which give a proof time of between 90% and 105% of the proof time given by a control baker's yeast produced from the *Saccharomyces cerevisiae* strain No. I-4341 by multiplication with adaptation to the presence of calcium propionate of said strain.

* * * * *